(12) United States Patent
Leonard et al.

(10) Patent No.: US 9,649,404 B2
(45) Date of Patent: May 16, 2017

(54) BONE FILLING CEMENT

(75) Inventors: Alain Leonard, Caixon (FR); Claudine Lavergne, Caixon (FR); Cyril Sender, Toulouse (FR); Benoit Donazzon, Toulouse (FR)

(73) Assignee: TEKNIMED, Vic-en-Bigorre (FR)

( * ) Notice: Subject to any disclaimer, the term of this patent is extended or adjusted under 35 U.S.C. 154(b) by 0 days.

(21) Appl. No.: 12/398,634

(22) Filed: Mar. 5, 2009

(65) Prior Publication Data
US 2010/0228358 A1 Sep. 9, 2010

(51) Int. Cl.
C08G 18/10 (2006.01)
A61L 24/00 (2006.01)
A61L 24/04 (2006.01)

(52) U.S. Cl.
CPC ......... *A61L 24/001* (2013.01); *A61L 24/0073* (2013.01); *A61L 2400/06* (2013.01); *A61L 2430/02* (2013.01)

(58) Field of Classification Search
USPC ............................... 433/228.1; 523/116, 219
See application file for complete search history.

(56) References Cited

U.S. PATENT DOCUMENTS

| 3,919,773 | A | * | 11/1975 | Freeman | ................... | 433/175 |
| 4,462,394 | A | * | 7/1984 | Jacobs | ..................... | 606/94 |
| 4,491,987 | A | * | 1/1985 | Park | .................... | 623/23.59 |
| 5,343,877 | A | * | 9/1994 | Park | .................... | 128/898 |
| 2005/0256220 | A1 | * | 11/2005 | Lavergne et al. | ............ | 523/115 |
| 2008/0248086 | A1 | * | 10/2008 | Asgari | .................. | 424/426 |
| 2009/0270527 | A1 | * | 10/2009 | Lin et al. | ...................... | 523/116 |

FOREIGN PATENT DOCUMENTS

| EP | 1592463 A1 | * | 11/2005 |
| EP | 1949918 A2 | * | 7/2008 |
| WO | WO 2004071543 A1 | * | 8/2004 |
| WO | WO 2007087400 A2 | * | 8/2007 |
| WO | WO 2008/109045 A2 | | 9/2008 |
| WO | WO 2008127290 A2 | * | 10/2008 |
| WO | WO 2009073193 A2 | * | 6/2009 |

OTHER PUBLICATIONS

Boesel et al., A Review on the Polymer Properties of Hydrophilic, Partially Degradable and Bioactive Acrylic Cements (HDBC), Progress in Polymer Science, Pergamon Press, Oxford, GB., vol. 33, No. 2, Jan. 19, 2008 pp. 180-190.

Kim et al., "The Characteristics of a Hydroxyapatite-Chitosan-PMMA Bone Cement", Biomaterials, Elsevier Science Publishers BV, Barking, vol. 25, No. 26, Nov. 1, 2004, pp. 5715-5723.

* cited by examiner

*Primary Examiner* — Peter A Salamon
(74) *Attorney, Agent, or Firm* — Birch, Stewart, Kolasch & Birch, LLP

(57) ABSTRACT

The present invention relates to an injectable bone cement for filling bones with mechanical properties equivalent to those of vertebral spongy bone comprising 70 to 99 wt. % of an acrylic polymer combined with an inorganic type radiopaque compound and 1 to 30 wt. % of calibrated hydrophilic flexible solid particles, said calibrated hydrophilic flexible solid particles being chosen from gelatin, poly(glycerol sebacate) or a mixture thereof.

A bone cement according to the invention is particularly intended for vertebroplasty, kyphoplasty or cementoplasty.

12 Claims, 1 Drawing Sheet

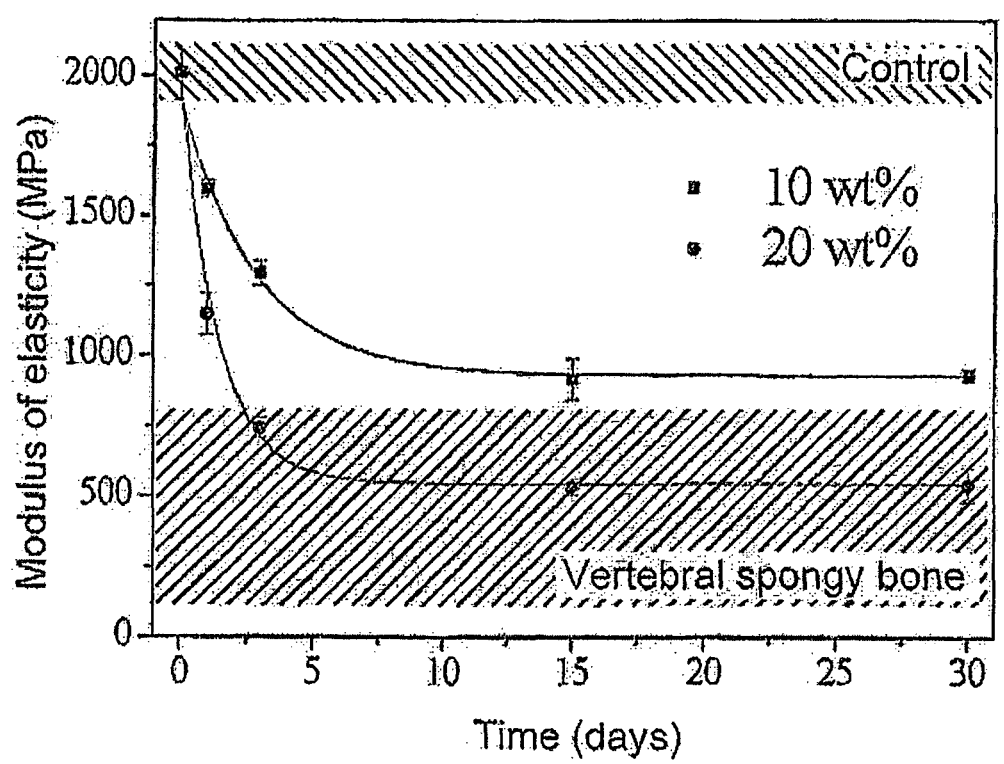

BONE FILLING CEMENT

FIELD OF THE INVENTION

The present invention relates to the field of polymeric cements, in particular acrylic cements, used to repair bone and joint traumatisms.

BACKGROUND OF THE INVENTION

The object of the invention is to provide a fluid cement for medical use having mechanical properties suited to filling spongy bone tissue, as well as a binary composition intended for the preparation of such a cement.

Bone cements have been used for many years to promote the fixation of artificial implants to the skeleton. The cement used as junction between the bone and the implant has to meet a number of requirements. In particular it has to be non toxic and biocompatible. Some cements have even been studied for their bioactive properties, in other words their action promoting adhesion and cell growth on the implant.

Since the mid 1980s, the use of cements has extended to bone repair and first of all percutaneous vertebroplasty. This minimally invasive technique enables a cement to be injected through a trocar into a fractured vertebra to provide bone volume and stabilization. The first percutaneous vertebroplasty was performed in 1984 and has since seen increasing success, opening the way to the plastic repair of other types of bone.

In the United States, between 400,000 and 500,000 clinical osteoporetic vertebral fractures occur every year. Approximately one third of these patients develop a debilitating chronic pain that does not respond to conservative treatment. For many people, this marks the end of an independent way of life. Such patients may be successfully treated through the percutaneous injection of bone cement into the fractured vertebral body. In this technique, a surgical cement paste is carefully injected by percutaneous route, by means of a long canulla, directly into the spongy bone of the fractured vertebral body. The main benefit of this technique lies in the fact that up to 90% of patients feel a relief of pain within 24 hours. (Jensen, M. E. et al. (1997). Am. J. Neuroradiol. 18, 1897-1904).

The cements used until now have been organic polymers, formed from a mixture of a prepolymer, generally PMMA (poly(methyl methacrylate)) and a monomer, generally MMA (methyl methacrylate), reacting in the presence of a polymerization activator.

Most commercially available cements are packaged in the form of two separate components: a powder mainly comprising beads of prepolymer and a liquid mainly containing the monomer. The initiator, for example benzoyl peroxide (BPO), is generally incorporated in the powder, whereas the liquid contains a chemical activator (catalyst) such as dimethyl-para-toluidine (DMPT), the polymerization reaction starting when the two components are mixed together. Further, in order to avoid any spontaneous polymerization that could occur during storage, a stabilizer, usually hydroquinone, is incorporated in the liquid component. The activator and the initiator are introduced in an amount of 0.2 to 2.5% in the corresponding component, the stabilizer for its part being effective at a few tens of ppm.

In order to visualize the cement during and after the operation by radiological means, a radiopaque substance may be added to the powder of prepolymer beads, usually barium sulfate ($BaSO_4$) or zirconium dioxide ($ZrO_2$).

These binary compositions for the preparation of bone cements, originally developed for the fixation of implants and the sealing of prostheses, meet the mechanical criteria of flexural and compressive strength, chemical neutrality and biocompatibility. They are approved for medical use and have proven their long term properties when the skeleton is subjected to considerable and repeated stresses. It is for this reason that bone cements for the fixation of implants have been considered as favored materials for bone reconstructive surgery and, in particular, in vertebroplasty or kyphoplasty.

Although this technique is employed more and more widely, concerns are been raised as regard the associated risks, and particularly fractures of vertebrae adjacent to the cemented vertebral bodies. This is one of the most serious usual complications, entailing a new vertebroplasty procedure. Apart from the volume and the distribution of the injected cement, which play important roles in re-establishing the mechanical properties of the fractured vertebral bodies (Liebschner M. A., et al. (2001) Spine 26, 1547-54), the high stiffness of cements compared to the trabecular vertebral bone is considered as one of the main risk factors in fracturing levels adjacent to the cemented bodies (Zoarski G. H., et al. (2002) J. Vasc. Interv. Radiol. 13, 139-148, Baroud G. et al. (2006) Joint Bone Spine 73, 144-150).

The cementation of a fractured vertebra results in a redistribution of the stress field within the treated vertebra and adjacent vertebral bodies, which is at the origin of subsequent fractures [Fribourg D., et al. (2004) Spine 29, 2270-76, Liebschner M. A., et al. (2001) Spine 26, 1547-54, Baroud G., et al. (2003) Comp. Methods Biomech. Biomed. Eng. 6, 133-39, Polikeit A., et al. (2003) Spine, 28(10), 991-96]. The presence of a cemented vertebra in a functional vertebral unit (two adjacent vertebral bodies and an intervertebral disc) has the effect of significantly reducing its fracture strength by 19% on average, the fracture systematically occurring in a non-cemented vertebral body (Berlemann U., et al. (2002) J. Bone Joint Surg. Br. 84, 748-52).

This result supports other biomechanical studies that have shown that the injection of acrylic cements into an isolated and non-fractured vertebra increases its compressive strength and its compression stiffness (Liebschner M. A., et al. (2001) Spine 26, 1547-54, Belkoff S. M., et al. (1999) Bone 25, 23S-26S, Wilson D. R., et al. (2000) Spine 25, 158-65, Belkoff S. M., et al. (2000) Spine 25, 1061-64, Heini P. F., et al. (2001) Eur. Spine J. 10, 164-71]. Finite element modeling has demonstrated an increase in the compression stiffness of adjacent vertebral bodies ranging between 13 and 18%, and in the hydrostatic pressure within intervertebral discs of about 11% following simulation of a vertebroplasty operation with an acrylic cement (Baroud G., et al. (2003) Comp. Methods Biomech. Biomed. Eng. 6, 133-39, Polikeit A., et al. (2003) Spine, 28(10), 991-96, Baroud G., et al. (2003) Eur. Spine J. 12, 421-26).

An increase in the discal pressure has been evidenced (Ananthakrishnan D., et al. (2003) Annual meeting of the American Academy of Orthopaedic Surgeons, New Orleans, 472) and may be explained by a deformation of the curvature and a reduction in the compliance of the vertebral end plates of the increased vertebrae (Baroud G., et al. (2003) Comp. Methods Biomech. Biomed. Eng. 6, 133-39). A recent biomechanical study concerned with the evolution of the mechanical properties of functional vertebral units constituted of three vertebrae and two discs has shown that the vertebral end plates of cemented vertebrae fracture systematically, unlike the functional control units (Moore S., et al. (2008) Griboi 2008, Montreal, Canada, p 22).

Existing acrylic cements allow mechanical properties that meet the prevailing regulatory requirements. However, these requirements have been established for cements for which the specific indications are the fixation of implants or the sealing of prostheses and for which the criteria in terms of mechanical properties are not suited to vertebroplasty, kyphoplasty or cementoplasty. The elastic modulus and the mechanical strength of cements based on acrylic resins required by the standards are very high compared to the mechanical properties of human spongy bone. This difference in mechanical impedance has been identified as a risk factor increasing the occurrence of fractures of vertebrae adjacent to the cemented vertebral bodies.

The stiffness of a structure may be linked to its modulus of elasticity or Young's modulus, a physical value easily determined by those skilled in the art. Static compression measurements on human vertebral spongy bone have made it possible to determine a Young's modulus between 100 and 800 MPa, the value being dependent on the bone density, the orientation of the trabeculae, the sample preparation, etc., whereas conventional vertebroplasty cements have values between 1,800 and 2,500 MPa. The modulus of elasticity and the mechanical compressive strength of human vertebral spongy bone are respectively 20 and 36 times lower on average compared to the acrylic cements currently injected by vertebroplasty or kyphoplasty (Hou F. J., et al. (1998) J. Biomech. 31, 1009-15, Fyhrie D. P. et al. (2000) Bone 26(2), 169-73, Banse X., et al. (2002) J. Bone & Mineral Res. 17(9), 1621-28, Shim V. P. W., et al. (2005) Int. J. Impact Eng. 32, 525-540).

In order to eliminate this mechanical disparity, the mechanical properties of PMMA cements must be adjusted to those of vertebral spongy bone. The result would then be a better distribution of stresses and thus a notable reduction in the risk of adjacent fractures.

The implementation conditions of cements in percutaneous surgery imply that the injectability criteria of the bone cement must be met on penalty of accidents, the effects of which may be dramatic for the patient such as paraplegia. For this reason, the practitioner needs to have a cement sufficiently fluid for it to be able to flow through a trocar of a few millimeters diameter and for it to retain this fluidity long enough for the practitioner to have the time to operate with full peace of mind.

Furthermore, the injected cement, even in small quantities, must be able to be visualized permanently during the operation by fluoroscopy.

Another serious drawback lies in the fact that the polymerization reaction of acrylic bone cements is exothermic, the temperature being liable to exceed 80° C. at the core of the cement in the vertebral body. Indeed, whereas in arthroplasty the thickness of acrylic cement forming the junction between the bone and the prosthesis does not exceed a few millimeters, enhancing the dissipation of the heat generated by the polymerization reaction, in vertebroplasty it can be more than one centimeter. This configuration has the consequence of limiting the dissipation of the calories generated and thereby contributing to a considerable rise in temperature at the core of the cement. This excessive temperature leads to a necrosis of the neighboring tissues. A temperature not exceeding 50 to 60° C. is preferable for the injection of surgical cements.

Thus, currently known cements, although they are efficient for the stabilization of fractures of osteoporotic vertebral bodies by percutaneous route, do not take into account the biomechanical specificities behind the phenomenon of adjacent fractures.

The prior art has demonstrated the existence of a composition that partially attempts to meet this problem. It involves an injectable mixture comprising a conventional two component powder/liquid bone cement, a third component comprising a hydrophilic liquid, non miscible with the cement, and an organic type X-ray contrast agent preferably in the form of an aqueous solution that can completely replace said third liquid component non miscible with the cement (EP1592463B1).

The non miscible liquid component is adapted to come out at the washout of said mixture, resulting in an interconnected porous bone replacement material. The resulting porosity has the effect of reducing the stiffness of the polymerized mixture to a level comparable to that of spongy bone.

The choice of the authors not to use a hydrophilic inorganic solid contrast agent such as barium sulfate ($BaSO_4$) or zirconium oxide ($ZrO_2$) is explained by the use of a third aqueous liquid component and to obtain an interconnected porosity according to their invention. Indeed, a selective accumulation of these contrast agents in the aqueous phase would result, after washout, in the release of particles of $BaSO_4$ or $ZrO_2$ into the body at a high level of toxicity. This phenomenon is favored by the interconnectivity of the pores, which enables an easy elimination of the particles present within the injectable mixture towards the body via the free circulation of physiological fluids. In terms of biocompatibility, the reduction in the stiffness of the polymerized mixture by the creation of an open and interconnected porosity by means of a third hydrophilic liquid component cannot therefore be conceived in the presence of a powdery solid contrast agent. It is for this reason that it is claimed to use an organic contrast agent in aqueous solution based on iodine and reaching 20% by weight of the injectable mixture. Nevertheless, those skilled in the art can easily recognize that the maximum iodinated contrast agent content disclosed in patent EP1592463B1 does not make it possible to obtain a contrast as high as through the use of solid contrast agents such as $BaSO_4$ or $ZrO_2$ that may currently be used up to 60% by weight of surgical cements in vertebroplasty or kyphoplasty.

Furthermore, in order that the polymerized cement is always radiopaque after washout of the contrast agent contained in the liquid component non miscible with the cement, it is disclosed that a lipophilic contrast agent miscible in the PMMA phase may be added. The addition of a fourth component to this formulation only makes its preparation more difficult.

Thus, certain requirements linked to the use of an acrylic cement for filling bone tissue in terms of fluoroscopic visualization of the cement during the surgical operation and while monitoring patients, ease of preparation, and effectiveness of the third phase introduced into the cement to promote the creation of a controlled porous structure (control of the size and the dispersion of the pores formed) are not fully resolved by the invention of patent EP1592463B1.

The object of the present invention is a bone cement suitable for use in bone reconstruction surgery, especially for filling a vertebral body, which makes it possible to meet the abovementioned requirements that are not fulfilled by the creation of a composite bone substitution structure composed of a matrix of identical composition to a radiopaque bone cement and with a homogeneous dispersion of zones of lower density and controlled dimensions. This composite structure allows a stiffness equivalent to or slightly greater than that of human vertebral spongy bone.

BRIEF DESCRIPTION OF THE DRAWINGS

The invention will be understood from the following description, considered with the accompanying drawing in which:

The FIGURE is a graph illustrating the modulus of elasticity (Young's Modulus) as a function of time for examples of a bone cement prepared in accordance with the present invention.

DESCRIPTION OF EXEMPLARY EMBODIMENTS

The specification of the bone cement according to the invention is as follows:
Injectability,
Setting time greater than or equal to 15 minutes,
Fluoroscopy opaque during and after injection,
Low exothermicity (polymerization temperature below 60° C.),
Young's modulus of compression less than 1,500 MPa.

The expression "setting time" refers to the time defined in the ISO 5833 Standard, Annex C.

Such a cement must be compatible with medical use from the point of view of its toxicity and its biocompatibility.

In the present invention, it has been found that it is possible to formulate a bone cement with stiffness equivalent to or slightly greater than that of human vertebral spongy bone from an acrylic cement based on poly(methyl methacrylate) and methyl methacrylate monomer meeting the above specifications, by introducing into said acrylic cement a homogeneous dispersion of zones of controlled dimensions and density less than the acrylic cement, while at the same time keeping the properties required in terms of biocompatibility, injectability, setting time, exothermicity, radiopacity in interventional surgery.

In the cement of the present invention, the zones of controlled dimensions and of density less than the acrylic cement are constituted of calibrated hydrophilic flexible solid particles of gelatin, poly(glycerol sebacate) or a mixture thereof. Gelatin is a substance of animal origin used in the composition of medical devices available on the market, poly(glycerol sebacate), or PGS, is a synthetic, biocompatible, bioresorbable and hydrophilic elastomer having mechanical properties similar to medical devices containing gelatin such as the diaphyseal obturator CEMSTOP®. PGS is a flexible elastomer at human physiological temperature. The particles of gelatin or PGS have the advantage of reducing the modulus of elasticity of cements without modifying the ease of injection and the radiopacity characteristics of acrylic cements in vertebroplasty. Indeed, the particles of gelatin and/or PGS dispersed in the cement allow to create a flexible composite material, the mechanical properties of which mimic those of vertebral spongy bone, contrary to the products currently on the market which allow much superior mechanical properties. The known biocompatibility of cements on the one hand, and gelatin or PGS on the other hand, imparts to their mixture a guaranteed biocompatibility.

More specifically, the aim of the present invention is an injectable bone cement for filling bones with mechanical properties equivalent to those of vertebral spongy bone comprising 70 to 99% by weight of an acrylic polymer combined with an inorganic type radiopaque compound and 1 to 30% by weight of calibrated hydrophilic flexible solid particles. The bone cement according to the present invention is medical grade and finds particularly advantageous applications in vertebroplasty, kyphoplasty or cementoplasty.

The hydrophilic flexible solid particles of gelatin and/or PGS are added in proportions ranging from 1 to 30% by total weight of cement. Preferably, a quantity between 10 and 20% by total weight of cement is chosen.

Hydrophilic flexible solid particles particularly suited to the preparation of the bone cement according to the present invention are of substantially spherical shape, of average diameter between 50 and 1,000 µm. Preferably, the average diameter of the particles is greater than 300 µm. Indeed, the applicant of the present invention has demonstrated that, up to 300 µm, the smaller the dimensions of the hydrophilic flexible solid particles (the higher the specific surface), the greater the quantity of liquid monomer adsorbed by said particles during preparation of the cement, the lower the quantity of monomer available for the partial dissolution of the beads of poly(methyl methacrylate) prepolymer and the more difficult it is to obtain a fluid cement. This difficulty could be overcome by a higher provision of liquid monomer but this would increase the residual content of monomer in the hardened cement, thus the release rate of monomer into the body and consequently the toxicity level of the cement. Needle-shaped or straw-shaped hydrophilic particles are further objects of the present invention.

Unexpectedly, it has been found that the calibrated hydrophilic flexible solid particles fulfill another particularly interesting function in the cement according to the invention. Indeed, it has been observed that the presence of calibrated hydrophilic solid particles brings about a reduction in the maximum temperature reached during the polymerization of the cement. The smaller the dimensions of the hydrophilic solid particles and the higher their quantity by total weight of cement, the greater this effect. Without going into theoretical studies, it is assumed that the calibrated hydrophilic solid particles act as heat dissipators. The result of this reduction in polymerization temperature, which can reach several tens of degrees Celsius compared to acrylic cements known from the prior art, is a reduction or even an absence of necrosis of the biological tissues in contact with the cement.

The applicant has shown that the presence of calibrated hydrophilic flexible solid particles homogeneously dispersed in the acrylic cement progressively reduces the stiffness of the hardened mixture according to the invention. The progressive diffusion of physiological liquids within the polymerized acrylic cement and their consecutive absorption by the hydrophilic flexible solid particles leads to a progressive and controlled reduction, followed by a stabilization of its stiffness at a level identical to or slightly greater than that of the vertebral spongy bone into which it is injected. The evolution over time of the mechanical properties of the mixture according to the present invention is linked to the reduction in the density of the zones occupied by the solid particles having absorbed the physiological liquids and not to the progressive creation of a porosity. As opposed to the creation of an open and interconnected porosity as disclosed in patent EP1592463B1 ending up with a bone substitution structure, the stiffness of which is immediately stable over time after injection of the cement and washout of the fluid component, the use of hydrophilic flexible solid particles as disclosed according to the present invention makes it possible to reduce the stiffness of acrylic cements in a progressive and controlled manner. The stiffness of the cement just after its injection is identical to the bone cements currently known in vertebroplasty, ensuring a stabilization of the fracture and an immediate antalgic effect. The final stabilized stiffness is identical to that of human vertebral spongy bone and contributes to reducing the risk of fracture of vertebrae adjacent to the cemented vertebrae.

Another advantage of the present invention is to impart the surgical cements a stiffness equivalent to that of vertebral spongy bone by using a lower volume fraction of calibrated hydrophilic flexible particles in comparison to the third liquid component claimed in patent EP1592463B1. Indeed, at identical volume fraction, the gelatin particles reduce the stiffness of acrylic cements more without creating open and interconnected porosity, which moreover increases the specific surface of acrylic implants and consequently the risks of generation and dissemination of debris from the implant or of release of cement components in toxic amounts in the body.

Although the biocompatibility or the recognition of acrylic cements by bone cells have been improved by the introduction into formulations of osteoconducting particles such as calcium phosphates, a mechanical biointegration has never been observed. An advantageous characteristic of the invention is the creation of a porosity at the surface of the cement in contact with the bone. This surface porosity due to the biodegradation of calibrated hydrophilic flexible solid particles entering into contact with the physiological fluids and the calcified tissues would enable a bone regrowth in the pores thereby created and would ensure the mechanical biointegration of the cement within the vertebral body.

The acrylic polymer according to the invention is composed of at least one poly(methyl methacrylate) (or PMMA) prepolymer and at least one methyl methacrylate (or MMA) monomer commonly used for the preparation of acrylic cements. Copolymers based on methyl methacrylate—styrene can also fall within the scope of the present invention. The prepolymer powders are provided as beads. The molar mass of these powders ranges between 150,000 and 1,500,000 g/mol. The average diameter of the particles ranges between 30 µm and 150 µm. The monomer is the methyl ester of methacrylic acid. Monomers and prepolymers such as MMA, PMMA and MMA-styrene copolymers for medical use are commercially available.

According to a preferred characteristic of the present application, the inorganic radiopaque compound is present in the acrylic cement and thus present throughout the life of the implant. This allows to visually monitor the injection of the cement to prevent any risk of extra-osseous leakage, and makes it possible to conduct post-operative medical monitoring. The radiopaque compound may be chosen from known compounds compatible with medical use. Preferably, it is chosen from the group composed of barium sulfate and zirconium dioxide. Barium sulfate ($BaSO_4$) is a radioopacifier commonly used in cements for the fixation of implants, the innocuousness of which is recognized. It generally comes in powder form, in which the particles have an average diameter of 1 to 10 µm. Zirconium dioxide ($ZrO_2$) may be used as an alternative. It is introduced in powder form, in which the particles have an average diameter of 20 µm.

For applications in vertebroplasty or kyphoplasty, the radiopaque composition represents an important fraction of the cement. Its purpose is to inject the cement under continuous fluoroscopic control. It may be constituted of a radiopaque compound, pure or as a mixture with other ingredients. A calcium phosphate, in particular a phosphocalcic hydroxyapatite of formula $Ca_{10}(PO_4)_6(OH)_2$ may advantageously be used. The introduction of calcium phosphate into the composition provides a twofold beneficial effect, firstly by improving the homogeneity of the cement and later its malleability, and secondly by increasing its biocompatibility. Indeed, it is known that hydroxyapatite favors bone regrowth by stimulating the biological activity of osteoblasts and their proliferation. It has been studied in this respect, although without its mechanical properties being profitably employed. Alternatively, in the present invention, the hydroxyapatite may be replaced by a tricalcic phosphate (TCP). Advantageously, the radiopaque composition present in the cement according to the invention comprises a radiopaque compound and calcium phosphate.

The cement according to the invention may finally contain a number of reagents favoring polymerization control. In particular, it may comprise, further to the ingredients cited above, an effective quantity of one or several of the following reagents: a chemical polymerization activator, a polymerization initiator, a stabilizer. Those skilled in the art know these reagents and how best to use them.

A reaction initiator may advantageously be chosen from polymerization catalysts such as benzoyl peroxide (BPO). The polymerization reaction activator or accelerator is preferably N,N-dimethyl-para-toluidine (DMPT). The stabilizer, preferably hydroquinone, may be added to avoid the premature polymerization of the monomer due to exposure to heat or light. These reagents are efficient at very low concentrations, which those skilled in the art know how to adjust as a function of the required kinetics.

The introduction of calibrated hydrophilic flexible solid particles into the cement has consequential effects on its physical and chemical characteristics, particularly its injectability, its polymerization kinetics, as well as its mechanical properties. The bone cement according to the invention has, in particular, a Young's modulus less than 1,500 MPa. To obtain optimal functional properties, the ingredient ratios as defined by the present application must be respected.

The present invention thus disclosed is suitable for medical use within the context of filling bones in various parts of the human body. However, on account of its mechanical properties, it finds a particularly advantageous application in the case of percutaneous vertebroplasties or kyphoplasties where the cement is injected through a trocar into a fractured vertebral body.

The cement according to the invention has good fluidity in the minutes after the ingredients have been brought into contact and may be worked for up to 15 minutes or even more after its preparation. The polymerization reaction between poly(methyl methacrylate) and the monomer brings about the solidification of the cement. The temperature in the vertebral body during polymerization is less than 60° C. In the present application, the term "cement" or "fluid cement" corresponds to the cement as it appears after mixing the ingredients. The composition of the cement will be considered as that of the ready to use fluid cement, prior to solidification.

A bone cement according to the invention may be obtained by the preparation of a binary composition resulting from the mixture of a powder phase P mainly comprising poly(methyl methacrylate) with a liquid phase L mainly comprising methyl methacrylate monomer in a P/L ratio between 3 and 4.6. Preferably, P/L is between 3.4 and 4.

The calibrated flexible solid particles are equally well incorporated in one or the other of the two phases P or L. Preferably, they are incorporated in the powder phase P.

The poly(methyl methacrylate) prepolymer powder, the methyl methacrylate monomer and the radiopaque composition on the one hand, and the hydrophilic flexible solid particles on the other hand, are advantageously provided in a weight ratio between 2 and 100. Preferably said ratio is between 4 and 9. Thus, it has been determined that the optimal formulation is that in which the proportion of cement is least and for which the mechanical properties are the lowest, adapted to those of vertebral spongy bone.

The binary composition according to the invention preferably comprises an effective quantity of one or several of the following reagents:

in the liquid component L, a chemical polymerization activator and a stabilizer;

in the powder component P, a polymerization initiator.

For example, the liquid component L may comprise from 0.7% to 2.5% of DMPT and 20 ppm of hydroquinone. The powder component P may comprise from 0.2% to 2% of benzoyl peroxide. Preferably, the liquid component L contains 1% of DMPT, while the powder component P contains between 0.3% and 0.35% of benzoyl peroxide.

When used in the operating theater, the two powder and liquid components are mixed together. At this moment, the powder phase partially dissolves in the liquid phase, thereby giving a mixture that has to be sufficiently fluid to be able to be injected into a vertebral body. During mixing, the activator and the initiator react to produce free radicals. These radicals initiate the polymerization reaction, leading to the progressive hardening of the cement, according to the required kinetics.

Once ready, the cement according to the invention will react to form a solid mass in a relatively short lapse of time (from several minutes to several tens of minutes), the formulation claimed here setting in not less than 15 minutes. It is obvious that the ingredients reacting together have to be mixed only at the time of use. For this reason it is useful to avail of a binary composition constituted of two pre-mixes of ingredients that simply have to be combined to prepare the cement according to the invention. These pre-mixes, one in powder form P mainly containing the poly(methyl methacrylate) prepolymer, the other in liquid form L mainly containing the methyl methacrylate monomer, constitute the two components of said binary composition.

The device according to the invention may advantageously be used for the preparation of a fluid cement for medical use for filling the vertebral body.

According to an advantageous alternative embodiment, the powder component P comprises 1% to 36% of flexible particles, preferably between 13% and 25% by weight relative to the weight of powder.

The following examples will make it easier to understand the invention, without however limiting its scope.

The following abbreviations are used:

PMMA:
poly(methyl methacrylate)
MMA:
methyl methacrylate
BPO:
benzoyl peroxide
$BaSO_4$:
barium sulfate
$ZrO_2$:
zirconium dioxide
HAP:
phosphocalcic hydroxyapatite
DMTP:
dimethyl-para-toluidine
HQ:
hydroquinone
P/L:
powder phase/liquid phase ratio, by weight.

Example 1: Binary Composition with 13% by Weight of Gelatin Relative to the Weight of Powder, (10% by Weight of Gelatin, Relative to the Weight of Cement)

| Powder phase (wt. %) | |
|---|---|
| PMMA | 43 |
| BPO | 0.4 |
| $ZrO_2$ | 39.2 |
| HAP | 4.4 |
| Gelatin | 13 |
| Liquid phase (wt. %) | |
| MMA | 99 |
| DMPT | 1 |
| HQ | 20 ppm | where P/L = 3.4
Final Young's modulus = 1,000 MPa

Example 2: Binary Composition with 25% by Weight of Gelatin Relative to the Weight of Powder, (20% by Weight of Gelatin, Relative to the Weight of Cement)

| Powder phase (wt. %) | |
|---|---|
| PMMA | 37.1 |
| BPO | 0.4 |
| $ZrO_2$ | 33.7 |
| HAP | 3.8 |
| Gelatin | 25 |
| Liquid phase (wt. %) | |
| MMA | 99 |
| DMPT | 1 |
| HQ | 20 ppm | where P/L = 4
Final Young's modulus = 500 MPa

Example 3: Method of Preparing a Bone Cement with Suitable Stiffness

Powder Component:

The powder phase is obtained by mixing the various ingredients.

Liquid Component:

The liquid phase is prepared by dissolving hydroquinone in the methyl methacrylate monomer. The stirring is maintained up to complete dissolution. DMPT is then added.

The two phases are packaged separately in containers suited to their conservation. The instantaneous preparation kits comprise a container containing the liquid phase and a container containing the powder phase.

Binary Composition

During use in the operating theater, the containers are opened and their contents are mixed together. The powder dissolves rapidly in the liquid phase, giving a fluid mixture that is injected into the vertebral body of the patient through suitable tubing. The BPO initiator and the DMPT activator react to form free radicals that initiate the polymerization reaction of the cement. The surgeon then has at least fifteen or so minutes to operate, continuously controlling the procedure by fluoroscopy.

Example 4: Tests as per the ISO 5833 Standard

The ISO 5833 Standard, entitled "Implants for surgery—Acrylic resin cements" defines the characteristics required by regulations and the standard tests enabling these characteristics to be quantified. The compositions described in the above mentioned examples 1 and 2 were tested to determine their setting time and the maximum temperature reached during polymerization.

The results obtained for the two compositions of examples 1 and 2 as well as the gelatin-free control composition are shown in Table 1.

All of the procedures are described in detail in the ISO 5833 Standard.

TABLE 1

| Composition | Setting time (min) | Maximum temperature (° C.) |
|---|---|---|
| Example 1 | 20.26 ± 0.44 | 52.0 ± 3.2 |
| Example 2 | 19.96 ± 0.43 | 47.2 ± 2.0 |
| Control | 18.24 ± 0.24 | 69.3 ± 2.1 |

It should be noted that their characteristics meet the specifications defined previously for bone cements used in percutaneous vertebroplasty (setting time greater than 15 minutes, fluoroscopy opaque).

Example 5: Mechanical Properties

A second series of tests relates to the mechanical properties of the installed cement, in other words its Young's modulus of compression. This parameter has been determined at regular intervals (4, 24 hours, 3, 8 and 14 days) on test specimens conditioned as per the ISO 5833 Standard and placed in distilled water at 37° C. under slow stirring. The results obtained with the compositions cited in example 1 and 2 and the gelatin-free control cement are shown in FIG. 1. For comparison, it will be recalled that the Young's modulus of compression of human vertebral spongy bone is between 100 and 800 Mpa.

What is claimed is:

1. A binary composition for the preparation of a fluid, injectable bone cement for filling bones with mechanical properties equivalent to those of vertebral spongy bone, said fluid, injectable bone cement having a Young's modulus of less than 1500 megapascals, wherein said binary composition comprises:
    a liquid phase L comprising a methyl methacrylate monomer; and
    a powder phase P comprising 70 to 99% by weight of a poly(methyl methacrylate) prepolymer combined with an inorganic type radiopaque compound and 1 to 30% by weight of calibrated hydrophilic flexible solid particles having an average diameter between 300 and 1,000 μm,
    wherein the P:L ratio in said binary composition is between 3 and 4.6 and
    wherein the weight ratio of (a) the poly(methyl methacrylate) prepolymer powder, the methyl methacrylate monomer, and the radiopaque component to (b) the hydrophilic flexible solid particles ranges from 2:1 to 100:1.

2. The binary composition according to claim 1, wherein the calibrated hydrophilic flexible solid particles are chosen from gelatin, poly(glycerol sebacate) or a mixture thereof.

3. The binary composition according to claim 1, comprising 10 to 20% by weight of calibrated hydrophilic flexible solid particles.

4. The binary composition according to claim 1, wherein the inorganic radiopaque compound is barium sulfate or zirconium dioxide.

5. The binary composition according to claim 1, wherein the inorganic radiopaque compound is combined with a calcium phosphate.

6. The binary composition according to claim 1, wherein
    the liquid phase L further comprises a chemical polymerization activator and a stabilizer and
    the powder phase P further comprises a polymerization initiator.

7. Binary composition according to claim 1, wherein the P/L ratio is between 3.4 and 4.

8. Binary composition according to claim 1, wherein the weight ratio of (a) the poly(methyl methacrylate) prepolymer powder, the methyl methacrylate monomer and the radiopaque composition to (b) the hydrophilic flexible solid particles ranges from 4:1 to 9:1.

9. A method for filling a bone defect by injection of an injectable fluid bone cement, which method comprises steps of:
    preparing a binary composition according to claim 1;
    preparing a bone cement by mixing said powder phase P with said liquid phase L to form a bone cement; and
    injecting the bone cement into said bone defect.

10. The binary composition according to claim 2, comprising 10 to 20% by weight of calibrated hydrophilic flexible solid particles.

11. The binary composition according to claim 6, comprising:
    dimethyl-para-toluidine as a chemical polymerization activator;
    benzoyl peroxide as a polymerization initiator; and
    hydroquinone as a stabilizer.

12. A composition comprising a liquid phase L and a powder phase P, said composition comprising:
    a liquid phase L comprising a methyl methacrylate, a chemical polymerization activator, and a stabilizer; and
    a powder phase P comprising 70 to 99% by weight of a poly(methyl methacrylate) polymer, a polymerization initiator, a barium sulfate and/or zirconium dioxide radiopaque compound, and 1 to 30% by weight of calibrated hydrophilic flexible solid gelatin and/or poly(glycerol sebacate) particles having an average diameter between 300 and 1000 μm, wherein the P:L ratio in said binary composition is between 3 and 4.6 and
    wherein the weight ratio of (a) the poly(methyl methacrylate) prepolymer powder, the methyl methacrylate monomer, and the radiopaque component to (b) the hydrophilic flexible solid particles ranges from 2:1 to 100:1.

* * * * *